United States Patent
Hsieh et al.

(10) Patent No.: US 8,338,158 B2
(45) Date of Patent: Dec. 25, 2012

(54) CIS-ACONITATE DECARBOXYLASE MUTANTS HAVING IMPROVED ENZYMATIC ACTIVITY

(75) Inventors: Hsin-Ju Hsieh, Hsinchu (TW); Pei-Ching Chang, Jhubei (TW); Kelly Teng, San Diego, CA (US)

(73) Assignee: Industrial Technology Research Institute, Hsinchu (TW)

( * ) Notice: Subject to any disclaimer, the term of this patent is extended or adjusted under 35 U.S.C. 154(b) by 446 days.

(21) Appl. No.: 12/624,658

(22) Filed: Nov. 24, 2009

(65) Prior Publication Data

US 2010/0330632 A1 Dec. 30, 2010

Related U.S. Application Data

(63) Continuation-in-part of application No. 12/494,487, filed on Jun. 30, 2009, now abandoned.

(51) Int. Cl.
*C12N 9/88* (2006.01)
*C12N 15/60* (2006.01)

(52) U.S. Cl. ...................... 435/232; 536/23.2

(58) Field of Classification Search .......... None
See application file for complete search history.

(56) References Cited

U.S. PATENT DOCUMENTS 7,479,381 B1 1/2009 Kuo et al.

FOREIGN PATENT DOCUMENTS

| EP | 2 017 344 | 1/2009 |
|---|---|---|
| JP | 2008-182936 | 8/2008 |
| JP | 2009-027999 | 2/2009 |
| WO | WO 2009/014437 | 1/2009 |

OTHER PUBLICATIONS

Uniprot Accession No. Q0C8L3 (May 2007).*
Shin Kanamasa et al., "Cloning and Functional Characterization of the *cis*-aconitic acid decarboxylase (CAD) gene from *Aspergillus terreus*"; Applied Microbiology and Biotechnology, vol. 80, No. 2, pp. 223-229 (2008).

* cited by examiner

*Primary Examiner* — Rebecca Prouty
(74) *Attorney, Agent, or Firm* — Occhiuti Rohlicek & Tsao LLP

(57) ABSTRACT

Cis-aconitate decarboxylase mutants having one or more mutations in a C-terminal region as compared with a wild-type cis-aconitate decarboxylase of *Aspergillus terreus*.

5 Claims, No Drawings

CIS-ACONITATE DECARBOXYLASE MUTANTS HAVING IMPROVED ENZYMATIC ACTIVITY

RELATED APPLICATION

This application is a continuation-in-part application of U.S. application Ser. No. 12/494,487, filed on Jun. 30, 2009, now abandoned, the content of which is hereby incorporated by reference in its entirety.

BACKGROUND OF THE INVENTION

Itaconic acid (IA), an essential compound used in manufacture of various products (e.g., acrylic fibers, rubbers, artificial diamonds, and lens), is highly demanded in the chemical industry. Certain microorganisms, such as *Aspergillus terreus*, produce this compound. It has been found that cis-aconitate decarboxylase (CAD) plays the key role in the biosynthesis of this compound.

SUMMARY OF THE INVENTION

The present invention is based on an unexpected discovery that genetically modified *Aspergillus* stains containing CAD mutants that carry one or more mutations in a C-terminal region produce higher levels of IA as compared with wild-type *Aspergillus*.

Accordingly, one aspect of this invention features an isolated polypeptide having the amino acid sequence of a mutated CAD that has a mutation in the region corresponding to 441-490 (e.g., 461-490 or 481-490) of the amino acid sequence of a wild-type CAD (SEQ ID NO:1). The mutation can be located at the position corresponding to position 490 in SEQ ID NO:1. In one example, this mutation is substitution of a peptide fragment (e.g., GI or GIK) for V at position 490 in SEQ ID NO:1. The mutated CAD described above can further include a mutation at the position corresponding to position 489 in SEQ ID NO:1 (e.g., L at position 489 in SEQ ID NO:1 being replaced with F). In another example, the mutation is substitution of the 441-490 fragment in SEQ ID NO:1 with another fragment, e.g., 441-492 in SEQ ID NO:9. Examples of the CAD mutants described herein include, but are not limited to, a polypeptide having the amino acid sequence of SEQ ID NO:3, 5, 7 or 9.

Another aspect of this invention features a nucleic acid encoding any of the polypeptides disclosed above and host cells containing the nucleic acid, which is in operative linkage with a promoter functional in the host cell. A promoter sequence is a nucleotide sequence containing an element(s) necessary for initiating transcription of an operably linked nucleic acid sequence. At a minimum, a promoter contains an RNA polymerase binding site. It can further contain one or more enhancer elements that enhance transcription, or contain one or more regulatory elements that control the on/off status of the promoter.

Also within the scope of this invention is a method for producing IA by culturing the host cell disclosed above in a suitable medium to allow production of IA. The IA thus produced can be isolated from the culture medium.

The details of one or more embodiments of the invention are set forth in the description below. Other features or advantages of the present invention will be apparent from the following detailed description of several examples, and also from the appended claims.

DETAILED DESCRIPTION OF THE INVENTION

Described herein is a mutated CAD that displays higher enzymatic activity relative to its wild-type counterpart.

CAD, which converts cis-aconitic acid to itaconic acid, is the key enzyme involved in the biosynthesis of IA. The term "CAD" used herein refers to any naturally occurring CADs (i.e., wild-type CAD). One example is the *A. terreus* CAD described in Dwiarti et al., J. Bioscience and Bioengineering, 94 (1):29-33, 2002 and WO 2009/014437). Provided below are the amino acid sequence (SEQ ID NO:1) of this *A. terreus* CAD and an example of its encoding nucleotide sequence (SEQ ID NO:2):

```
Amino Acid and Nucleotide Sequences of A. terrues CAD atgaccaaacaatctgcggacagcaacgcaaagtcaggagttacgtccgaaatatgtcat
 M  T  K  Q  S  A  D  S  N  A  K  S  G  V  T  S  E  I  C  H
tgggcatccaacctggccactgacgacatcccttcggacgtattagaaagagcaaaatac
 W  A  S  N  L  A  T  D  D  I  P  S  D  V  L  E  R  A  K  Y
cttattctcgacggtattgcatgtgcctgggttggtgcaagagtgccttggtcagagaag
 L  I  L  D  G  I  A  C  A  W  V  G  A  R  V  P  W  S  E  K
tatgttcaggcaacgatgagctttgagccgccgggggcctgcagggtgattggatatgga
 Y  V  Q  A  T  M  S  F  E  P  P  G  A  C  R  V  I  G  Y  G
cagaaactggggcctgttgcagcagccatgaccaattccgctttcatacaggctacggag
 Q  K  L  G  P  V  A  A  A  M  T  N  S  A  F  I  Q  A  T  E
cttgacgactaccacagcgaagcccccctacactctgcaagcattgtccttcctgcggtc
 L  D  D  Y  H  S  E  A  P  L  H  S  A  S  I  V  L  P  A  V
tttgcagcaagtgaggtcttagccgagcagggcaaaacaatttccggtatagatgttatt
 F  A  A  S  E  V  L  A  E  Q  G  K  T  I  S  G  I  D  V  I
ctagccgccattgtggggtttgaatctggcccacggatcggcaaagcaatctacggatcg
 L  A  A  I  V  G  F  E  S  G  P  R  I  G  K  A  I  Y  G  S
gacctcttgaacaacggctggcattgtggagctgtgtatggcgctccagccggtgcgctg
 D  L  L  N  N  G  W  H  C  G  A  V  Y  G  A  P  A  G  A  L
gccacaggaaagctcctcggtctaactccagactccatggaagatgctctcggaattgcg
 A  T  G  K  L  L  G  L  T  P  D  S  M  E  D  A  L  G  I  A
tgcacgcaagcctgtggtttaatgtcggcgcaatacggaggcatggtaaagcgtgtgcaa
 C  T  Q  A  C  G  L  M  S  A  Q  Y  G  G  M  V  K  R  V  Q
cacggattcgcagcgcgtaatggtcttcttggggggactgttggcccatggtgggtacgag
 H  G  F  A  A  R  N  G  L  L  G  G  L  L  A  H  G  G  Y  E
gcaatgaaaggtgtcctggagagatcttacggcggtttcctcaagatgttcaccaagggc
 A  M  K  G  V  L  E  R  S  Y  G  G  F  L  K  M  F  T  K  G
aacggcagagagcctccctacaaagaggaggaagtggtggctggtctcggttcattctgg
 N  G  R  E  P  P  Y  K  E  E  E  V  V  A  G  L  G  S  F  W
```

-continued

```
cataccttractattcgcatcaagctctatgcctgctgcggacttgtccatggtccagtc
 H  T  F  T  I  R  I  K  L  Y  A  C  C  G  L  V  H  G  P  V
gaggctatcgaaaaccttcaggggagataccccgagctcttgaatagagccaacctcagc
 E  A  I  E  N  L  Q  G  R  Y  P  E  L  L  N  R  A  N  L  S
aacattcgccatgttcatgtacagctttcaacggcctcgaacagtcactgtggatgata
 N  I  R  H  V  H  V  Q  L  S  T  A  S  N  S  H  C  G  W  I
ccagaggagagaccatcagttcaatcgcagggcagatgagtgtcgcatacattctcgcc
 P  E  E  R  P  I  S  S  I  A  G  Q  M  S  V  A  Y  I  L  A
gtccagctggtcgaccagcaatgtcttttgtcccagttttctgagtttgatgacaacctg
 V  Q  L  V  D  Q  Q  C  L  L  S  Q  F  S  E  F  D  D  N  L
gagaggccagaagtttgggatctggccaggaaggttacttcatctcaaagcgaagagtt
 E  R  P  E  V  W  D  L  A  R  K  V  T  S  S  Q  S  E  E  F
gatcaagacggcaactgtctcagtgcgggtcgcgtgaggattgagttcaacgatggttct
 D  Q  D  G  N  C  L  S  A  G  R  V  R  I  E  F  N  D  G  S
tctattacggaaagtgtcgagaagcctcttggtgtcaaagagcccatgccaaacgaacgg
 S  I  T  E  S  V  E  K  P  L  G  V  K  E  P  M  P  N  E  R
attctccacaaataccgaacccttgctggtagcgtgacggacgaatcccgggtgaaagag
 I  L  H  K  Y  R  T  L  A  G  S  V  T  D  E  S  R  V  K  E
attgaggatctttgtcctcggcctggacaggctcaccgacattagcccattgctggagctg
 I  E  D  L  V  L  G  L  D  R  L  T  D  I  S  P  L  L  E  L
ctgaattgccccgtgaaatcgccactggtataa     (SEQ ID NO: 2)
 L  N  C  P  V  K  S  P  L  V  -       (SEQ ID NO: 1)
```

Other natural CADs are polypeptides found in non-*A. terreus* species that possess the same enzymatic activity. These polypeptides are highly homologous to the *A. terreus* CAD described above, i.e., having an amino acid sequence at least 75% (85%, 90%, or 95%) identical to SEQ ID NO:1. The amino acid sequences and their encoding gene sequences can be retrieved from gene/protein databases, e.g., GenBank, using SEQ ID NOs:1 and 2 as queries.

The percent identity of two amino acid sequences is determined using the algorithm of Karlin and Altschul *Proc. Natl. Acad. Sci. USA* 87:2264-68, 1990, as modified in Karlin and Altschul *Proc. Natl. Acad. Sci. USA* 90:5873-77, 1993. Such an algorithm is incorporated into the BLASTN and BLASTX programs (version 2.0) of Altschul, et al. *J. Mol. Biol.* 215: 403-10, 1990. BLAST protein searches can be performed with the BLASTX program, score=50, wordlength=3 to obtain amino acid sequences homologous to the protein molecules of the invention. Where gaps exist between two sequences, Gapped BLAST can be utilized as described in Altschul et al., *Nucleic Acids Res.* 25:3389-3402, 1997. When utilizing BLAST and Gapped BLAST programs, the default parameters of the respective programs (e.g., BLASTX and BLASTN) can be used.

The CAD mutant of this invention contains one or more mutations in the region of a naturally-occurring CAD that corresponds to 441-490 in SEQ ID NO:1. The one or more mutations can be deletion, insertion, or amino acid residue substitution (e.g., a fragment being replaced with a single amino acid residue or with another fragment, or a single residue being replaced with a fragment). Listed below are a number of exemplary CAD mutants, including their amino acid sequences (mutated positions bold-faced) and encoding nucleotide sequences:

```
mCAD1:
atgaccaaacaatctgcggacagcaacgcaaagtcaggagttacgtccgaaatatgtcat
 M  T  K  Q  S  A  D  S  N  A  K  S  G  V  T  S  E  I  C  H
tgggcatccaacctggccactgacgacatcccttcggacgtattagaaagagcaaaatac
 W  A  S  N  L  A  T  D  D  I  P  S  D  V  L  E  R  A  K  Y
cttattctcgacggtattgcatgtgcctgggttggtgcaagagtgccttggtcagagaag
 L  I  L  D  G  I  A  C  A  W  V  G  A  R  V  P  W  S  E  K
tatgttcaggcaacgatgagctttgagccgccgggggcctgcagggtgattggatatgga
 Y  V  Q  A  T  M  S  F  E  P  P  G  A  C  R  V  I  G  Y  G
cagaaactggggcctgttgcagcagccatgaccaattccgctttcatacaggctacggag
 Q  K  L  G  P  V  A  A  A  M  T  N  S  A  F  I  Q  A  T  E
cttgacgactaccacagcgaagcccccctacactctgcaagcattgtccttcctgcggtc
 L  D  D  Y  H  S  E  A  P  L  H  S  A  S  I  V  L  P  A  V
tttgcagcaagtgaggtcttagccgagcagggcaaaacaatttccggtatagatgttatt
 F  A  A  S  E  V  L  A  E  Q  G  K  T  I  S  G  I  D  V  I
ctagccgccattgtggggtttgaatctggcccacggatcggcaaagcaatctacggatcg
 L  A  A  I  V  G  F  E  S  G  P  R  I  G  K  A  I  Y  G  S
gacctcttgaacaacggctggcattgtggagctgtgtatggcgctccagccggtgcgctg
 D  L  L  N  N  G  W  H  C  G  A  V  Y  G  A  P  A  G  A  L
gccacaggaaagctcctcggtctaactccagactccatggaagatgctctcggaattgcg
 A  T  G  K  L  L  G  L  T  P  D  S  M  E  D  A  L  G  I  A
tgcacgcaagcctgtggtttaatgtcggcgcaatacggaggcatggtaaagcgtgtgcaa
 C  T  Q  A  C  G  L  M  S  A  Q  Y  G  G  M  V  K  R  V  Q
cacggattcgcagcgcgtaatggtcttcttggggactgttggcccatggtgggtacgag
 H  G  F  A  A  R  N  G  L  L  G  G  L  L  A  H  G  G  Y  E
gcaatgaaaggtgtcctggagagatcttacggcggtttcctcaagatgttcaccaagggc
 A  M  K  G  V  L  E  R  S  Y  G  G  F  L  K  M  F  T  K  G
aacggcagagagcctccctacaaagaggaggaagtggtggctggtctcggttcattctgg
 N  G  R  E  P  P  Y  K  E  E  E  V  V  A  G  L  G  S  F  W
```

-continued

```
cataccttactattcgcatcaagctctatgcctgctgcggacttgtccatggtccagtc
 H  T  F  T  I  R  I  K  L  Y  A  C  C  G  L  V  H  G  P  V
gaggctatcgaaaaccttcaggggagataccccgagctcttgaatagagccaaccttcagc
 E  A  I  E  N  L  Q  G  R  Y  P  E  L  L  N  R  A  N  L  S
aacattcgccatgttcatgtacagctttcaacggcctcgaacagtcactgtggatggata
 N  I  R  H  V  H  V  Q  L  S  T  A  S  N  H  C  G  W  I
ccagaggagagacccatcagttcaatcgcagggcagatgagtgtcgcatacattctcgcc
 P  E  E  R  P  I  S  S  I  A  G  Q  M  S  V  A  Y  I  L  A
gtccagctggtcgaccagcaatgtcttttgtcccagttttctgagtttgatgacaacctg
 V  Q  L  V  D  Q  Q  C  L  L  S  Q  F  S  E  F  D  D  N  L
gagaggccagaagtttgggatctggccaggaaggttacttcatctcaaagcgaagagttt
 E  R  P  E  V  W  D  L  A  R  K  V  T  S  S  Q  S  E  E  F
gatcaagacggcaactgtctcagtgcgggtcgcgtgaggattgagttcaacgatggttct
 D  Q  D  G  N  C  L  S  A  G  R  V  R  I  E  F  N  D  G  S
tctattacggaaagtgtcgagaagcctcttggtgtcaaagagcccatgccaaacgaacgg
 S  I  T  E  S  V  E  K  P  L  G  V  K  E  P  M  P  N  E  R
attctccacaaataccgaacccttgctggtagcgtgacggacgaatcccgggtgaaagag
 I  L  H  K  Y  R  T  L  A  G  S  V  T  D  E  S  R  V  K  E
attgaggatcttgtcctcggcctggacaggctcaccgacattagcccattgctggagctg
 I  E  D  L  V  L  G  L  D  R  L  T  D  I  S  P  L  L  E  L
ctgaattgccccgtgaaatcgccccttggtatataa    (SEQ ID NO: 4)
 L  N  C  P  V  K  S  P  L  G  I  -      (SEQ ID NO: 3)
``` mCAD2

```
atgaccaaacaatctgcggacagcaacgcaaagtcaggagttacgtccgaaatatgtcat
 M  T  K  Q  S  A  D  S  N  A  K  S  G  V  T  S  E  I  C  H
tgggcatccaacctggccactgacgacatcccttcggacgtattagaaagagccaaaatac
 W  A  S  N  L  A  T  D  D  I  P  S  D  V  L  E  R  A  K  Y
cttattctcgacggtattgcatgtgcctggggttggtgcaagagtgccttggtcagagaag
 L  I  L  D  G  I  A  C  A  W  V  G  A  R  V  P  W  S  E  K
tatgttcaggcaacgatgagctttgagccgccgggggcctgcagggtgattggatatgga
 Y  V  Q  A  T  M  S  F  E  P  P  G  A  C  R  V  I  G  Y  G
cagaaactggggctgttgcagcagccatgaccaattccgctttcatacaggctacggag
 Q  K  L  G  P  V  A  A  A  M  T  N  S  A  F  I  Q  A  T  E
cttgacgactaccacagcgaagccccctacactctgcaagcattgtccttcctgccggtc
 L  D  D  Y  H  S  E  A  P  L  H  S  A  S  I  V  L  P  A  V
tttgcagcaagtgaggtcttagccgagcagggcaaaacaatttccggtatagatgttatt
 F  A  A  S  E  V  L  A  E  Q  G  K  T  I  S  G  I  D  V  I
ctagccgccattgtggggtttgaatctggcccacggatcggcaaagcaatctacggatcg
 L  A  A  I  V  G  F  E  S  G  P  R  I  G  K  A  I  Y  G  S
gacctcttgaacaacggctggcattgtggagctgtgtatggcgctccagccggtgcgctg
 D  L  L  N  N  G  W  H  C  G  A  V  Y  G  A  P  A  G  A  L
gccacaggaaagctcctcggtctaactccagactccatggaagatgctctcggaattgcg
 A  T  G  K  L  L  G  L  T  P  D  S  M  E  D  A  L  G  I  A
tgcacgcaagcctgtggtttaatgtcggcgcaatacggaggcatggtaaagcgtgtgcaa
 C  T  Q  A  C  G  L  M  S  A  Q  Y  G  G  M  V  K  R  V  Q
cacggattcgcagcgcgtaatggtcttcttggggactgttggcccatggtgggtacgag
 H  G  F  A  A  R  N  G  L  L  G  G  L  L  A  H  G  G  Y  E
gcaatgaaaggtgtcctggagagatcttacggcggtttcctcaagatgttcaccaagggc
 A  M  K  G  V  L  E  R  S  Y  G  G  F  L  K  M  F  T  K  G
aacggcagagagcctccctacaaagaggaggaagtggtggctggtctcggttcattctgg
 N  G  R  E  P  P  Y  K  E  E  E  V  V  A  G  L  G  S  F  W
cataccttactattcgcatcaagctctatgcctgctgcggacttgtccatggtccagtc
 H  T  F  T  I  R  I  K  L  Y  A  C  C  G  L  V  H  G  P  V
gaggctatcgaaaaccttcaggggagataccccgagctcttgaatagagccaaccttcagc
 E  A  I  E  N  L  Q  G  R  Y  P  E  L  L  N  R  A  N  L  S
aacattcgccatgttcatgtacagctttcaacggcctcgaacagtcactgtggatggata
 N  I  R  H  V  H  V  Q  L  S  T  A  S  N  H  C  G  W  I
ccagaggagagacccatcagttcaatcgcagggcagatgagtgtcgcatacattctcgcc
 P  E  E  R  P  I  S  S  I  A  G  Q  M  S  V  A  Y  I  L  A
gtccagctggtcgaccagcaatgtcttttgtcccagttttctgagtttgatgacaacctg
 V  Q  L  V  D  Q  Q  C  L  L  S  Q  F  S  E  F  D  D  N  L
gagaggccagaagtttgggatctggccaggaaggttacttcatctcaaagcgaagagttt
 E  R  P  E  V  W  D  L  A  R  K  V  T  S  S  Q  S  E  E  F
gatcaagacggcaactgtctcagtgcgggtcgcgtgaggattgagttcaacgatggttct
 D  Q  D  G  N  C  L  S  A  G  R  V  R  I  E  F  N  D  G  S
tctattacggaaagtgtcgagaagcctcttggtgtcaaagagcccatgccaaacgaacgg
 S  I  T  E  S  V  E  K  P  L  G  V  K  E  P  M  P  N  E  R
attctccacaaataccgaacccttgctggtagcgtgacggacgaatcccgggtgaaagag
 I  L  H  K  Y  R  T  L  A  G  S  V  T  D  E  S  R  V  K  E
attgaggatcttgtcctcggcctggacaggctcaccgacattagcccattgctggagctg
 I  E  D  L  V  L  G  L  D  R  L  T  D  I  S  P  L  L  E  L
ctgaattgccccgtgaaatcgcccctgggtataaaataa   (SEQ ID NO: 6)
 L  N  C  P  V  K  S  P  L  G  I  K  -     (SEQ ID NO: 5)
``` mCAD3:

```
atgaccaaacaatctgcggacagcaacgcaaagtcaggagttacgtccgaaatatgtcat
 M  T  K  Q  S  A  D  S  N  A  K  S  G  V  T  S  E  I  C  H
tgggcatccaacctggccactgacgacatcccttcggacgtattagaaagagcaaaatac
 W  A  S  N  L  A  T  D  D  I  P  S  D  V  L  E  R  A  K  Y
cttattctcgacgtattgcatgtgcctgggttggtgcaagagtgcctggtcagagaag
 L  I  L  D  G  I  A  C  A  W  V  G  A  R  V  P  W  S  E  K
tatgttcaggcaacgatgagctttgagccgccgggggcctgcagggtgattggatatgga
 Y  V  Q  A  T  M  S  F  E  P  P  G  A  C  R  V  I  G  Y  G
cagaaactggggcctgttgcagcagccatgaccaattccgctttcatacaggctacggag
 Q  K  L  G  P  V  A  A  A  M  T  N  S  A  F  I  Q  A  T  E
cttgacgactaccacagcgaagcccccctacactctgcaagcattgtccttcctgcggtc
 L  D  D  Y  H  S  E  A  P  L  H  S  A  S  I  V  L  P  A  V
tttgcagcaagtgaggtcttagccgagcagggcaaaacaatttccggtatagatgttatt
 F  A  A  S  E  V  L  A  E  Q  G  K  T  I  S  G  I  D  V  I
ctagccgccattgtggggtttgaatctggcccacggatcggcaaagcaatctacggatcg
 L  A  A  I  V  G  F  E  S  G  P  R  I  G  K  A  I  Y  G  S
gacctcttgaacaacggctggcattgtggagctgtgtatggcgctccagccggtgcgctg
 D  L  L  N  N  G  W  H  C  G  A  V  Y  G  A  P  A  G  A  L
gccacaggaaagctcctcggtctaactccagactccatggaagatgctctcggaattgcg
 A  T  G  K  L  L  G  L  T  P  D  S  M  E  D  A  L  G  I  A
tgcacgcaagcctgtggtttaatgtcggcgcaatacggaggcatggtaaagcgtgtgcaa
 C  T  Q  A  C  G  L  M  S  A  Q  Y  G  G  M  V  K  R  V  Q
cacggattcgcagcgcgtaatggtcttcttgggggactgttggcccatggtgggtacgag
 H  G  F  A  A  R  N  G  L  L  G  G  L  L  A  H  G  G  Y  E
gcaatgaaaggtgtcctggagagatcttacggcggtttcctcaagatgttcaccaagggc
 A  M  K  G  V  L  E  R  S  Y  G  G  F  L  K  M  F  T  K  G
aacggcagagagcctccctacaaagaggaggaagtggtggctggtctcggttcattctgg
 N  G  R  E  P  P  Y  K  E  E  E  V  V  A  G  L  G  S  F  W
catacctttactattcgcatcaagctctatgcctgctgcggacttgtccatggtccagtc
 H  T  F  T  I  R  I  K  L  Y  A  C  C  G  L  V  H  G  P  V gaggctatcgaaaaccttcaggggagataccccgagctcttgaatagagccaacctcagc
 E  A  I  E  N  L  Q  G  R  Y  P  E  L  L  N  R  A  N  L  S
aacattcgccatgttcatgtacagcttttcaacggcctcgaacagtcactgtggatggta
 N  I  R  H  V  Q  L  S  T  A  S  N  S  H  C  G  W  I
ccagaggagagacccatcagttcaatcgcagggcagatgagtgtcgcatacattctcgcc
 P  E  E  R  P  I  S  S  I  A  G  Q  M  S  V  A  Y  I  L  A
gtccagctggtcgaccagcaatgtcttttgtcccagttttctgagtttgatgacaacctg
 V  Q  L  V  D  Q  Q  C  L  L  S  Q  F  S  E  F  D  D  N  L
gagaggccagaagtttgggatctggccaggaaggttacttcatctcaaagcgaagagttt
 E  R  P  E  V  W  D  L  A  R  K  V  T  S  S  Q  S  E  E  F
gatcaagacggcaactgtctcagtgcgggtcgcgtgaggattgagttcaacgatggttct
 D  Q  D  G  N  C  L  S  A  G  R  V  R  I  E  F  N  D  G  S
tctattacgaaagtgtcgagaagcctcttggtgtcaaagagccatgccaaacgaacgg
 S  I  T  E  S  V  E  K  P  L  G  V  K  E  P  M  P  N  E  R
attctccacaaataccgaacccttgctggtagcgtgacggacgaatcccgggtgaaagag
 I  L  H  K  Y  R  T  L  A  G  S  V  T  D  E  S  R  V  K  E
attgaggatcttgtcctcggcctggacaggctcaccgacattagcccattgctggagctg
 I  E  D  L  V  L  G  L  D  R  L  T  D  I  S  P  L  L  E  L
ctgaattgcccccgtgaaatcgccctttggtatataa   (SEQ ID NO: 8)
 L  N  C  P  V  K  S  P  F  G  I  -    (SEQ ID NO: 7)
``` mCAD4

```
atgaccaagcagtctgctgattccaacgcgaagtctggtgtgacctctgagatctgtcac
 M  T  K  Q  S  A  D  S  N  A  K  S  G  V  T  S  E  I  C  H
tgggcgtctaatctcgccactgatgatatcccgagcgacgttctggagcgtgcaaaatac
 W  A  S  N  L  A  T  D  D  I  P  S  D  V  L  E  R  A  K  Y
ctgatcctggatgtatcgcgtgcgcgtgggtaggtgctcgtgtcccatggtctgaaaaa
 L  I  L  D  G  I  A  C  A  W  V  G  A  R  V  P  W  S  E  K
tacgttcaagcgaccatgtcttcgaacctccgggtgcgtgtcgtgtcatcggttacggc
 Y  V  Q  A  T  M  S  F  E  P  P  G  A  C  R  V  I  G  Y  G
cagaaactgggtccggtagcggctgccatgacgaactctgcatttattcaggcgaccgaa
 Q  K  L  G  P  V  A  A  A  M  T  N  S  A  F  I  Q  A  T  E
ctcgatgactatcactctgaagcgccgctgcattccgcgtctatcgttctcccggcagtt
 L  D  D  Y  H  S  E  A  P  L  H  S  A  S  I  V  L  P  A  V
ttcgcggcgagcgaagtactggccgaacagggtaaaaccatctctggtattgacgtgatt
 F  A  A  S  E  V  L  A  E  Q  G  K  T  I  S  G  I  D  V  I
ctggctgcgatcgttggtttcgagagcggtcctcgcatcggcaaagcgatctacggttct
 L  A  A  I  V  G  F  E  S  G  P  R  I  G  K  A  I  Y  G  S
gacctcctgaacaacggctggcactgcggtgcggtatatggcgcaccggctggtgcgctc
 D  L  L  N  N  G  W  H  C  G  A  V  Y  G  A  P  A  G  A  L
gcaactggtaagctcctgggcctcacgccggacagcatggaagatgcactgggtattgcc
 A  T  G  K  L  L  G  L  T  P  D  S  M  E  D  A  L  G  I  A
tgcacgcaagcatgcggcctcatgtccgcgcagtatggtggcatggttaaacgtgttcag
 C  T  Q  A  C  G  L  M  S  A  Q  Y  G  G  M  V  K  R  V  Q
cacggtttcgcagcgcgtaatggtctcctcggtggcctcctggctcacggcggctacgag
 H  G  F  A  A  R  N  G  L  L  G  G  L  L  A  H  G  G  Y  E
gcgatgaaaggtgttctcgagcgttcttacggtggcttcctgaagatgttcaccaagggc
 A  M  K  G  V  L  E  R  S  Y  G  G  F  L  K  M  F  T  K  G
aacggtcgtgaaccgccgtacaaagaagaagaggttgtggctggtctgggtagcttctgg
 N  G  R  E  P  P  Y  K  E  E  E  V  V  A  G  L  G  S  F  W
```

```
cacaccttcaccattcgtatcaaactgtacgcgtgctgcggtctcgtacacggtcctgtt
 H  T  F  T  I  R  I  K  L  Y  A  C  C  G  L  V  H  G  P  V
gaagccattgaaaacctccagggtcgttacccggaactgctcaatcgtgctaacctgtct
 E  A  I  E  N  L  Q  G  R  Y  P  E  L  L  N  R  A  N  L  S
aacatccgccacgttcacgtacaactctctaccgcgagcaactcccactgtggttggatc
 N  I  R  H  V  H  V  Q  L  S  T  A  S  N  S  H  C  G  W  I
ccagaagagcgcccaatctcttctatcgcgggtcaaatgtctgtcgcatatatcctcgcc
 P  E  E  R  P  I  S  S  I  A  G  Q  M  S  V  A  Y  I  L  A
gttcagctcgttgaccaacagtgtctgctcagccagttctccgagtttgacgataatctg
 V  Q  L  V  D  Q  Q  C  L  L  S  Q  F  S  E  F  D  D  N  L
gaacgcccggaagtgtgggacctggcacgtaaggttaccagctctcaatctgaggagttc
 E  R  P  E  V  W  D  L  A  R  K  V  T  S  S  Q  S  E  E  F
gaccaggacggtaactgtctctctgccggtcgcgtccgtattgagttcaacgacggctcc
 D  Q  D  G  N  C  L  S  A  G  R  V  R  I  E  F  N  D  G  S
tccatcaccgaatccgttgagaagccgctcggtgtaaaggaaccaatgccaaatgaacgc
 S  I  T  E  S  V  E  K  P  L  G  V  K  E  P  M  P  N  E  R
ttcccgcgtggtgaaccaggccagccacgtttctgcgaaaacgcgggaaaaagtggaagc
 F  P  R  G  E  P  G  Q  P  R  F  C  E  N  A  G  K  S  G  S
ggcgatggcggagctgaattacattcccaaccgcgtggcacaacaactggcgggcaaaca
 G  D  G  G  A  E  L  H  S  Q  P  R  G  T  T  T  G  G  Q  T
gtcgttgctgattggcgttgccacctccagtctggctaa (SEQ ID NO: 10)
 V  V  A  D  W  R  C  H  L  Q  S  G  -         (SEQ ID NO: 9)
```

Any of the above-mentioned CAD mutants can be prepared by conventional recombinant technology. For example, one or more mutations can be introduced into a nucleotide sequence encoding a wild-type CAD and the mutated encoding sequence can be expressed in a suitable host cell to produce the mutated CAD polypeptide. If desired, the coding sequences are subjected to codon optimization based on the optimal codon usage in the host microorganism. Below is an example of an *A. terreus* CAD coding sequence, in which certain codons were replaced with optimal *E. coli* codons:

```
                                           (SEQ ID NO: 11)
atgaccaagcagtctgctgattccaacgcgaagtctggtgtgacctct gagatctgtcactgggcgtctaatctcgccactgatgatatcccgagc gacgttctggagcgtgcaaaatacctgatcctggatggtatcgcgtgc gcgtgggtaggtgctcgtgtcccatggtctgaaaaatacgttcaagcg accatgtctttcgaacctccgggtgcgtgtcgtgtcatcggttacggc cagaaactgggtccggtagcggctgccatgacgaactctgcatttatt caggcgaccgaactcgatgactatcactctgaagcgccgctgcattcc gcgtctatcgttctcccggcagttttcgcggcgagcgaagtactggcc gaacagggtaaaaccatctctggtattgacgtgattctggctgcgatc gttggtttcgagagcggtcctcgcatcggcaaagcgatctacggttct gacctcctgaacaacggctggcactgcggtgcggtatatggcgcaccg gctggtgcgctcgcaactggtaagctcctgggcctcacgccggacagc atggaagatgcactgggtattgcctgcacgcaagcatgcggcctcatg tccgcgcagtatggtggcatggttaaacgtgttcagcacggtttcgca gcgcgtaatggtctcctcggtggcctcctggctcacggcggctacgag gcgatgaaaggtgttctcgagcgttcttacggtggcttcctgaagatg ttcaccaagggcaacggtcgtgaaccgccgtacaaagaagaagaggtt gtggctggtctgggtagcttctggcacaccttcaccattcgtatcaaa ctgtacgcgtgctgcggtctcgtacacggtcctgttgaagccattgaa aacctccagggtcgttacccggaactgctcaatcgtgctaacctgtct
```

```
                    -continued
aacatccgccacgttcacgtacaactctctaccgcgagcaactcccac tgtggttggatcccagaagagcgcccaatctcttctatcgcgggtcaa atgtctgtcgcatatatcctcgccgttcagctcgttgaccaacagtgt ctgctcagccagttctccgagtttgacgataatctggaacgcccggaa gtgtgggacctggcacgtaaggttaccagctctcaatctgaggagttc gaccaggacggtaactgtctctctgccggtcgcgtccgtattgagttc aacgacggctcctccatcaccgaatccgttgagaagccgctcggtgta aaggaaccaatgccaaatgaacgcatcctgcacaaataccgtaccctg gcgggttctgtaacggacgaaagccgtgttaaggagatcgaggatctc gtgctcggcctggaccgtctgaccgatattagcccgctcctcgagctg ctgaattgtccggttaaatcccactggtttaa
```

The level of protein expression can be measured by conventional methods. In one example, the levels of a wild-type and mutated CAD are determined by Western analysis. The increased enzymatic activity of the polypeptide can be confirmed by conventional methods. In one example, the IA level produced in the host cells can be determined by HPLC and an elevated level of IA production relative to the same type of host cells expressing a wild-type CAD indicates that the mutant CAD possesses improved enzymatic activity as compared with the wild-type CAD.

After its elevated enzymatic activity has been confirmed, the CAD mutant can be used for producing IA. More specifically, its coding sequence can be cloned into a suitable expression plasmid and introduced into a suitable host microorganism. The microorganism is then cultured in a suitable medium for itaconic acid production. Preferably, the medium contains glucose or citrate as the precursor for making itaconic acid. After a sufficient culturing period, the medium is collected and the secreted itaconic acid is isolated.

Without further elaboration, it is believed that one skilled in the art can, based on the above description, utilize the present invention to its fullest extent. The following specific example is, therefore, to be construed as merely illustrative, and not limitative of the remainder of the disclosure in any way whatsoever. All publications cited herein are incorporated by reference.

EXAMPLE 1

Itaconic Acid Production in *A. terreus* Strains Containing Mutated CADs

Generating *A. terreus* Mutants/Fusants Containing Mutated CADs

Mutants of *A. terreus* were generated by random mutagenesis as follows. *A. terreus* ATCC10020 cells at a concentration of $10^8$ cell/ml was incubated overnight in an IA producing medium (pH 2.8) that contains, in one liter distilled water, 100 g glucose, 6 g $(NH_4)_2SO_4$, 0.2 g $KH_2PO_4$, 1 g $MgSO_4.7H_2O$, 0.4 g $CaSO_4$, $0.5\times10^{-3}$ g $CuSO4$, $0.5\times10^{-3}$ g $ZnSO4.4H2O$, $3\times10^{-3}$ g $FeCl_3$. The cells were collected, washed, and then incubated with 10-15 g/l *Lysosome* (contains beta-glucanase, cellulose, protease and chitinase) and a mutagen, i.e., 1-methyl-3-nitro-nitrosoguanidine (NTG, 1-5 g/l) or ethylmethanesulfonate (EMS, 2-200 mg/l), to induce mutations. The cells were again collected and re-suspended in a medium, placed on a 2-deoxy-glucose (2-DG)-potato agar plate (2-DG concentration 0.25-5.0 g/l), and cultured under suitable conditions to allow colony formation. Around 12.5-99.3% ($3\times10^7$-$9\times10^8$ CFU/ml) of the cells died in the presence of either mutagen. Each of the surviving colonies were cultured in 25 ml of the above-described IA production medium at a concentration of $10^{10}$ cell/ml and then plated on an IA-potato dextrose agar plate containing a pH indicator (pH 3.0-5.4), which was selected from bromocresol green, bromophenol blue, or congo red (30-130 mg/L). Colonies producing high levels of IA were selected based on their color shown on the plate.

Mutants M1-M5 were selected in the just-described screening process as producing high levels of IA. These mutants were then cultured in the IA-production medium for 3.5 days and the levels of IA in the culture media, filtered through a membrane having a pore size of 0.22 μm, were analyzed by HPLC, using the LiChroCART column (5-mm particle size, 125-mm length, 4-mm diameter, E. Merck, Germany). IA was eluted at 30° C. with a buffer containing 20 mM ortho-phosphoric acid at a flow rate of 1 ml/min. The eluted IA was detected at 230 nm with a Shimadzu SD-20A Absorbance Detector (Shimadzu, Japan). As shown in Table 1 below, mutants M1-M5 produced higher levels of IA than wild-type *A. terreus*.

TABLE 1

Itaconic Acid Production by M1-M5

| Strains | IA concentration (g/l) | IA concentration (folds) | Yield (%) | Yield (folds) |
|---|---|---|---|---|
| WT | 10.87 | 1 | 23.38 | 1 |
| M1 | 17.43 | 1.60 | 28.30 | 1.21 |
| M2 | 17.12 | 1.57 | 29.06 | 1.24 |
| M3 | 21.68 | 1.99 | 33.55 | 1.44 |
| M4 | 28.04 | 2.58 | 36.85 | 1.58 |
| M5 | 23.51 | 2.16 | 39.32 | 1.68 |

*A. terreus* mutants were also generated by genome shuffling with *A. niger* as follows. *Aspergillus terreus* ATCC10020 cells ($10^8$ cell/ml) and *Aspergillus niger* NRRRL330 cells ($10^8$ cell/ml) were cultured separately overnight at 35° C. in a medium (pH 3) containing, in one liter distilled water, 150 g glucose, 2.5 g $(NH_4)_2SO_4$, 2 g $KH_2PO_4$, 0.5 g $MgSO_4$, $0.06\times10^{-3}$ g $CuSO_4.5H_2O$, $0.1\times10^{-3}$ g $ZnSO_4.7H2O$, $0.1\times10^3$ g $FeSO_4.24H_2O$. All cells were collected, washed with a phosphate buffer (pH 6) containing 0.7 M KCl, and incubated in *Lysosome* for 2 hours with gentle shaking. The protoplasts thus released were subjected to osmosis using 1.4 M sorbitol and then collected by centrifugation at 1800 g. The protoplasts were re-suspended in distilled water to form crude protoplast suspensions. Equal volumes of *A. terreus* and *A. niger* crude protoplast suspensions were mixed and centrifuged at 1000 g, 4° C. for 10 min. The protoplast pellet thus formed was resuspended in a 0.05 M glycin-NaOH buffer (pH7.5) containing 30% (w/v) polyethylene glycol (PEG) 6000, 100 mM $CaCl_2$, and 0.7 M KCl. The suspension was incubated at 30° C. for 20 min, plated onto the surface of a potato dextrose agar plate, and incubated at 30° C. for 5-7 days to allow formation of colonies, which were fusants. The fusion frequency in this study was found to be ~200 CFU/ml. Each of the fusants was then cultured in 25 ml of the IA production medium described above at 35° C. for 5.5 days in a rotary shaker (150 rev/min). Fusants G1-G6 were found to produce higher levels of IA than wild-type *A. terreus*.

TABLE 2

Itaconic Acid Production by G1-G6

| Strains | IA concentration (g/l) | IA concentration (folds) | Yield (%) | Yield (folds) |
|---|---|---|---|---|
| WT | 21.83 | 1 | 27.20 | 1 |
| G1 | 35.97 | 1.65 | 49.69 | 1.83 |
| G2 | 35.63 | 1.63 | 50.26 | 1.85 |
| G3 | 29.33 | 1.34 | 67.12 | 2.47 |
| G4 | 31.90 | 1.46 | 50.46 | 1.86 |
| G5 | 31.62 | 1.45 | 55.29 | 2.03 |
| G6 | 30.98 | 1.42 | 53.69 | 1.97 |

Determining Nucleotide Sequences Encoding CAD Mutants

The CAD genomic sequences of certain mutants/fusants were determined by conventional methods. Briefly, genomic DNAs and total RNAs were isolated from the mutants/fusants of interest using Wizard® Genomic DNA Purification kit (Promega, USA) and Epicentre® MasterPure™ RNA Purification kit (Biotechnologies, USA), respectively. A DNA fragment containing the CAD gene was amplified from the genomic DNAs by polymerase chain reaction (PCR) with tag polymerase (Invitrogen™, US) using the primers listed below:

```
CAD1 (forward):
5'-CAGCCATGACCAATTCCGCTTTCA-3'    (SEQ ID NO: 12)

CAD1 (reverse):
5'-AAGACCTCACTTGCTGCAAAGACC-3'    (SEQ ID NO: 13)

Cad-f-2 (504-523):
5'-TTGTGGAGCTGTGTATGGCG-3'        (SEQ ID NO: 14)

Cad-(700-716)-F:
5'-GTTGGCCCATGGTGGG-3'             (SEQ ID NO: 15)

Cad-(251-270)-R:
5'-CATGGCTGCTGCAACAGGCC-3'         (SEQ ID NO: 16)
```

The PCR conditions were: 94° C. for 5 s, 30 cycles of 94° C. for 20 s, 56° C. for 30 s, 72° C. for 2 min, and a final extension at 72° C. for 10 s.

The CAD coding sequences were also amplified by reverse transcription polymerase chain reaction (RT-PCR) using the total RNAs mentioned above as the template and the primers listed above with the Verso 1-step RT-PCR kit (AB gene, US) under the following conditions: 47° C. for 30 s, 94° C. for 2 min, 30 cycles of 94° C. for 20 s, 55° C. for 30 s, 72° C. for 2 min, and a final extension at 72° C. for 5 min.

Results obtained from this study indicate that M1 and M4 contain mCAD1, G2 and G4 contain mCAD2, and G3 contains mCAD3. The amino acid sequences and nucleotide sequences of these CAD mutants are shown in pages 4-7 above.

Determining Enzymatic Activity of CAD Mutants

The CAD activity of these mutated CAD were examined following the method described in Dwiarti et al., J. Bioscience and Bioengineering 94:29-33 (2002) with slight modifications. Briefly, A. terreus strains containing these CAD mutants were cultured in a suitable medium ($10^{10}$ cells/ml) for 3 days at 35° C. in a rotary shaker (150 rev/min). The cultured cells were harvested, suspended in a sodium phosphate buffer (0.2 M, pH 6.2) at a volume ratio of 1:10, and lyzed by pulsed sonication for 10 min to form crude lysates. The lysates were centrifuged and the resultant supernatants were collected. 4.5 ml of each supernatant were incubated with 0.5 ml of a solution containing cis-aconitic acid at a final concentration of 5.0 mM for 10 min at 40° C. The enzyme reaction was terminated by addition of 0.1 ml 12 M HCl into the reaction mixture. The amount of itaconic acid, the product of the enzymatic reaction, was measured by HPLC (column: LiChroCART, detector: SPD-20AD, 20 mM ortho-phosphoric acid, at 30° C., at 230 nm).

TABLE 3

CAD Activity in A. terreus Strains Containing Mutated CADs

| Strains | CAD activity (umol/mg/min) | CAD activity (folds) | CAD |
|---|---|---|---|
| WT | 0.007 | 1 | WT |
| M1 | 0.056 | 8 | mCAD1 |
| M4 | 0.064 | 9.1 | mCAD1 |
| G2 | 0.009 | 1.3 | mCAD2 |
| G3 | 0.008 | 1.1 | mCAD3 |
| G4 | 0.018 | 2.6 | mCAD2 |

As shown in Table 3 above, A. terreus strains containing the mutated CADs all exhibited increased CAD activity as compared with wild-type A. terreus.

EXAMPLE 2

Preparation of CAD Mutants in E. Coli mCAD1, mCAD2, and mCAD3 were amplified by PCR using primers list below:

```
CAD (forward):
actcatatgATGACCAAACAATCTGCGGA        (SEQ ID NO: 17)

mCAD1 (reverse):
tacggatcc TATACCAAGGGGCGATTTCAC      (SEQ ID NO: 18)

mCAD2 (reverse):
tacggatcc TTTTATACCCAGGGGCGATTTC     (SEQ ID NO: 19)

mCAD3 (reverse):
tacggatccTATACCAAAGGGCGATTTCACG      (SEQ ID NO: 20)
```

The PCR condition were as follows: 94° C. for 5 s, 25 cycles of 94° C. for 20 s, 56° C. for 30 s, 72° C. for 2 min, and a final extension at 72° C. for 10 s.

The PCR products were cloned into pET-24a DNA 69749-3 (Novagen), which carries a His-tag, via restriction sites BamHI and NdeI. The resultant plasmids were introduced into DH5α (GeneMark, Cat. No. DH01-10). Positive clones were determined by colony PCR, using the primers 5'-ctcagcttcctttcggcctt-3' (SEQ ID NO:21) and 5'-cgcacctgtg-gcgcc-3' (SEQ ID NO:22) and further confirmed by DNA sequencing. Plasmid DNAs carrying coding sequences for mCAD1, mCAD2, and mCAD3 were purified using Plasmid Miniprep Purification Kit (GeneMark, Cat. No: DP01-300).

mCAD1, mCAD2, and mCAD3, as well as wild-type (wt) CAD, were overexpressed in DH5α and purified using His Binding® Kits (Novagen, Cat. No. 70239-3). As confirmed by Westernblot, the expression levels of these mutants were similar to that of the wt CAD, indicating that the mutations had no impact on protein expression.

The CAD activities of the purified CAD mutants were examined following the method described in Example 1 above. As shown Table 4 below, the mutated CADs all exhibited increased CAD activity as compared with wt CAD.

TABLE 4

CAD Activity in E. Coli Containing Mutated CADs

| Strains | CAD activity (%) | CAD activity (folds) |
|---|---|---|
| WT | 100 | 1 |
| mCAD1 | 118.24 | 1.2 |
| mCAD2 | 153.88 | 1.5 |
| mCAD3 | 104.16 | 1.04 |

Moreover, enzyme kinetics was examined following the method described in Dwiarti et al., J. Bioscience and Bioengineering 94:29-33; 2002 with slight modifications. Briefly, an E. coli strain containing one of the CAD mutants was cultured in LB medium for a suitable period at 35° C. in a rotary shaker (250 rev/min). When the optical density of the culture reached 0.4, the bacterial cells were cultured in M9 medium (1 g/l yeast extract and 20 g/l glucose) supplemented with IPTG for 5-6 hours at 30° C. in a rotary shaker (250 rev/min) to allow expression of the CAD mutant. The cells were harvested, suspended in a sodium phosphate buffer (0.2 M, pH 6.5) at a volume ratio of 1:10, and lyzed by a bead beater for 1 min to form a crude lysate. The lysate was centrifuged and the resultant supernatant was collected. To determine the enzymatic activity of the CAD mutant, 0.5 ml of the supernatant was incubated with 0.5 ml of a solution containing cis-aconitic acid at a final concentration of 12 mM at 37° C. for various periods and then mixed with 1 μl 12 M HCl to terminate the enzymatic reaction. The amount of itaconic acid, converted from cis-aconitic acid by the CAD mutant, was measured by HPLC (column: LiChroCART, detector: SPD-20AD, 20 mM ortho-phosphoric acid, at 30° C., at 230 nm).

TABLE 5

Enzyme Kinetics of CAD Mutants

| | Km (mM) | Vm (mM/min) | Kcat (1/s) | kcat/Km (mM-1s-1) |
|---|---|---|---|---|
| WT | 5 | 0.0024 | 60.61 | 12.12 |
| mCAD3 | 3.7 | 0.002 | 81.82 | 22.11 |
| mCAD2 | 5 | 0.0027 | 72.73 | 14.55 |
| mCAD1 | 5.55 | 0.0025 | 75.76 | 13.65 |

In sum, the results from this study indicate that mCAD1, mCAD2, and mCAD3 exhibited higher enzymatic activity than wt CAD.

EXAMPLE 3

Itaconic Acid Production in E. Coli Expressing mCAD4 mCAD4 was generated by random mutagenesis as follows. Error-Prone PCR was performed using SEQ ID NO:11 as a template and the GeneMorph® II Random Mutagenesis Kit (Stratagene, Cat. No. 200550). A mutated sequence encoding mCAD4 was identified. Compared to wt CAD, mCAD4 contains a substituted fragment (52 amino acids) at positions 441-490 in wt CAD (SEQ ID NO:1).

IA production in *E. coli* strains expressing either mCAD4 or wt CAD was determined following the method described in Example 1 and the results are shown in Table 6 below:

TABLE 6

Itaconic Acid Production in *E. Coli* Strains Expressing mCAD4 and wt CAD

| Strains | IA concentration (g/l) | IA concentration (folds) |
|---------|------------------------|--------------------------|
| WT      | 0.020121               | 1                        |
| mCAD4   | 0.024648               | 1.22                     |

The above results indicate that an *E. coli* strain expressing mCAD4 produced a higher level of IA as compared to an *E. coli* strain expressing wt CAD. This indicates that mCAD4 possesses higher enzymatic activity than wt CAD.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. An isolated polypeptide, comprising the amino acid sequence of a mutated cis-aconitate decarboxylase (CAD), wherein the mutated CAD has a mutation in the region corresponding to positions 441-490 in the wild-type CAD sequence of SEQ ID NO:1, the amino acid sequence being that of SEQ ID NO: 3, 5, 7, or 9.

2. The isolated polypeptide of claim 1, wherein the amino acid sequence is that of SEQ ID NO:3.

3. The isolated polypeptide of claim 1, wherein the amino acid sequence is that of SEQ ID NO:5.

4. The isolated polypeptide of claim 1, wherein the amino acid sequence is that of SEQ ID NO:7.

5. The isolated polypeptide of claim 1, wherein the amino acid sequence is that of SEQ ID NO:9.

* * * * *

SEQUENCE LISTING

<160> NUMBER OF SEQ ID NOS: 22

<210> SEQ ID NO 1
<211> LENGTH: 490
<212> TYPE: PRT
<213> ORGANISM: Aspergillus terreus

<400> SEQUENCE: 1

```
Met Thr Lys Gln Ser Ala Asp Ser Asn Ala Lys Ser Gly Val Thr Ser
1               5                   10                  15

Glu Ile Cys His Trp Ala Ser Asn Leu Ala Thr Asp Asp Ile Pro Ser
            20                  25                  30

Asp Val Leu Glu Arg Ala Lys Tyr Leu Ile Leu Asp Gly Ile Ala Cys
        35                  40                  45

Ala Trp Val Gly Ala Arg Val Pro Trp Ser Glu Lys Tyr Val Gln Ala
    50                  55                  60

Thr Met Ser Phe Glu Pro Pro Gly Ala Cys Arg Val Ile Gly Tyr Gly
65                  70                  75                  80

Gln Lys Leu Gly Pro Val Ala Ala Ala Met Thr Asn Ser Ala Phe Ile
            85                  90                  95

Gln Ala Thr Glu Leu Asp Asp Tyr His Ser Glu Ala Pro Leu His Ser
        100                 105                 110

Ala Ser Ile Val Leu Pro Ala Val Phe Ala Ala Ser Glu Val Leu Ala
    115                 120                 125

Glu Gln Gly Lys Thr Ile Ser Gly Ile Asp Val Ile Leu Ala Ala Ile
130                 135                 140

Val Gly Phe Glu Ser Gly Pro Arg Ile Gly Lys Ala Ile Tyr Gly Ser
145                 150                 155                 160

Asp Leu Leu Asn Asn Gly Trp His Cys Gly Ala Val Tyr Gly Ala Pro
            165                 170                 175

Ala Gly Ala Leu Ala Thr Gly Lys Leu Leu Gly Leu Thr Pro Asp Ser
        180                 185                 190

Met Glu Asp Ala Leu Gly Ile Ala Cys Thr Gln Ala Cys Gly Leu Met
    195                 200                 205

Ser Ala Gln Tyr Gly Gly Met Val Lys Arg Val Gln His Gly Phe Ala
    210                 215                 220

Ala Arg Asn Gly Leu Leu Gly Gly Leu Leu Ala His Gly Gly Tyr Glu
225                 230                 235                 240
```

```
Ala Met Lys Gly Val Leu Glu Arg Ser Tyr Gly Gly Phe Leu Lys Met
                245                 250                 255

Phe Thr Lys Gly Asn Gly Arg Glu Pro Pro Tyr Lys Glu Glu Val
            260                 265                 270

Val Ala Gly Leu Gly Ser Phe Trp His Thr Phe Thr Ile Arg Ile Lys
        275                 280                 285

Leu Tyr Ala Cys Cys Gly Leu Val His Gly Pro Val Glu Ala Ile Glu
    290                 295                 300

Asn Leu Gln Gly Arg Tyr Pro Glu Leu Leu Asn Arg Ala Asn Leu Ser
305                 310                 315                 320

Asn Ile Arg His Val His Val Gln Leu Ser Thr Ala Ser Asn Ser His
                325                 330                 335

Cys Gly Trp Ile Pro Glu Glu Arg Pro Ile Ser Ser Ile Ala Gly Gln
            340                 345                 350

Met Ser Val Ala Tyr Ile Leu Ala Val Gln Leu Val Asp Gln Gln Cys
        355                 360                 365

Leu Leu Ser Gln Phe Ser Glu Phe Asp Asp Asn Leu Glu Arg Pro Glu
    370                 375                 380

Val Trp Asp Leu Ala Arg Lys Val Thr Ser Ser Gln Ser Glu Glu Phe
385                 390                 395                 400

Asp Gln Asp Gly Asn Cys Leu Ser Ala Gly Arg Val Arg Ile Glu Phe
                405                 410                 415

Asn Asp Gly Ser Ser Ile Thr Glu Ser Val Glu Lys Pro Leu Gly Val
            420                 425                 430

Lys Glu Pro Met Pro Asn Glu Arg Ile Leu His Lys Tyr Arg Thr Leu
        435                 440                 445

Ala Gly Ser Val Thr Asp Glu Ser Arg Val Lys Glu Ile Glu Asp Leu
    450                 455                 460

Val Leu Gly Leu Asp Arg Leu Thr Asp Ile Ser Pro Leu Leu Glu Leu
465                 470                 475                 480

Leu Asn Cys Pro Val Lys Ser Pro Leu Val
                485                 490

<210> SEQ ID NO 2
<211> LENGTH: 1473
<212> TYPE: DNA
<213> ORGANISM: Aspergillus terreus

<400> SEQUENCE: 2
atgaccaaac aatctgcgga cagcaacgca aagtcaggag ttacgtccga aatatgtcat      60
tgggcatcca acctggccac tgacgacatc ccttcggacg tattagaaag agcaaaatac    120
cttattctcg acggtattgc atgtgcctgg gttggtgcaa gagtgccttg gtcagagaag    180
tatgttcagg caacgatgag ctttgagccg ccggggcct gcagggtgat ggatatgga     240 cagaaactgg ggcctgttgc agcagccatg accaattccg ctttcataca ggctacggag    300
cttgacgact accacagcga agccccccta cactctgcaa gcattgtcct tcctgcggtc    360
tttgcagcaa gtgaggtctt agccgagcag ggcaaaacaa tttccggtat agatgttatt    420
ctagccgcca ttgtggggtt tgaatctggc ccacggatcg gcaaagcaat ctacggatcg    480
gacctcttga caacggctg cattgtgga gctgtgtatg cgctccagc cggtgcgctg      540 gccacaggaa agctcctcgg tctaactcca gactccatgg aagatgctct cggaattgcg    600
tgcacgcaag cctgtggttt aatgtcggcg caatacggag catggtaaa gcgtgtgcaa    660 cacggattcg cagcgcgtaa tggtcttctt gggggactgt tggcccatgg tgggtacgag    720
```

```
gcaatgaaag gtgtcctgga gagatcttac ggcggtttcc tcaagatgtt caccaagggc      780
aacggcagag agcctcccta caaagaggag gaagtggtgg ctggtctcgg ttcattctgg      840 catacccttta ctattcgcat caagctctat gcctgctgcg gacttgtcca tggtccagtc     900
gaggctatcg aaaaccttca ggggagatac cccgagctct tgaatagagc caacctcagc      960
aacattcgcc atgttcatgt acagctttca acggcctcga acagtcactg tggatggata     1020
ccagaggaga gacccatcag ttcaatcgca gggcagatga gtgtcgcata cattctcgcc     1080
gtccagctgg tcgaccagca atgtcttttg tcccagtttt ctgagtttga tgacaacctg     1140
gagaggccag aagtttggga tctggccagg aaggttactt catctcaaag cgaagagttt     1200
gatcaagacg gcaactgtct cagtgcgggt cgcgtgagga ttgagttcaa cgatggttct     1260
tctattacgg aaagtgtcga gaagcctctt ggtgtcaaag agcccatgcc aaacgaacgg     1320
attctccaca ataccgaac ccttgctggt agcgtgacgg acgaatcccg ggtgaaagag      1380
attgaggatc ttgtcctcgg cctggacagg ctcaccgaca ttagcccatt gctggagctg     1440
ctgaattgcc ccgtgaaatc gccactggta taa                                  1473
```

<210> SEQ ID NO 3
<211> LENGTH: 491
<212> TYPE: PRT
<213> ORGANISM: Aspergillus terreus

<400> SEQUENCE: 3

```
Met Thr Lys Gln Ser Ala Asp Ser Asn Ala Lys Ser Gly Val Thr Ser
1               5                   10                  15

Glu Ile Cys His Trp Ala Ser Asn Leu Ala Thr Asp Asp Ile Pro Ser
            20                  25                  30

Asp Val Leu Glu Arg Ala Lys Tyr Leu Ile Leu Asp Gly Ile Ala Cys
        35                  40                  45

Ala Trp Val Gly Ala Arg Val Pro Trp Ser Glu Lys Tyr Val Gln Ala
    50                  55                  60

Thr Met Ser Phe Glu Pro Pro Gly Ala Cys Arg Val Ile Gly Tyr Gly
65                  70                  75                  80

Gln Lys Leu Gly Pro Val Ala Ala Ala Met Thr Asn Ser Ala Phe Ile
                85                  90                  95

Gln Ala Thr Glu Leu Asp Asp Tyr His Ser Glu Ala Pro Leu His Ser
            100                 105                 110

Ala Ser Ile Val Leu Pro Ala Val Phe Ala Ala Ser Glu Val Leu Ala
        115                 120                 125

Glu Gln Gly Lys Thr Ile Ser Gly Ile Asp Val Ile Leu Ala Ala Ile
    130                 135                 140

Val Gly Phe Glu Ser Gly Pro Arg Ile Gly Lys Ala Ile Tyr Gly Ser
145                 150                 155                 160

Asp Leu Leu Asn Asn Gly Trp His Cys Gly Ala Val Tyr Gly Ala Pro
                165                 170                 175

Ala Gly Ala Leu Ala Thr Gly Lys Leu Leu Gly Leu Thr Pro Asp Ser
            180                 185                 190

Met Glu Asp Ala Leu Gly Ile Ala Cys Thr Gln Ala Cys Gly Leu Met
        195                 200                 205

Ser Ala Gln Tyr Gly Gly Met Val Lys Arg Val Gln His Gly Phe Ala
    210                 215                 220

Ala Arg Asn Gly Leu Leu Gly Gly Leu Leu Ala His Gly Gly Tyr Glu
225                 230                 235                 240

Ala Met Lys Gly Val Leu Glu Arg Ser Tyr Gly Gly Phe Leu Lys Met
```

```
                    245                 250                 255
Phe Thr Lys Gly Asn Gly Arg Glu Pro Pro Tyr Lys Glu Glu Val
            260                 265                 270
Val Ala Gly Leu Gly Ser Phe Trp His Thr Phe Thr Ile Arg Ile Lys
        275                 280                 285
Leu Tyr Ala Cys Cys Gly Leu Val His Gly Pro Val Glu Ala Ile Glu
        290                 295                 300
Asn Leu Gln Gly Arg Tyr Pro Glu Leu Leu Asn Arg Ala Asn Leu Ser
305                 310                 315                 320
Asn Ile Arg His Val His Val Gln Leu Ser Thr Ala Ser Asn Ser His
                325                 330                 335
Cys Gly Trp Ile Pro Glu Glu Arg Pro Ile Ser Ser Ile Ala Gly Gln
            340                 345                 350
Met Ser Val Ala Tyr Ile Leu Ala Val Gln Leu Val Asp Gln Gln Cys
        355                 360                 365
Leu Leu Ser Gln Phe Ser Glu Phe Asp Asp Asn Leu Glu Arg Pro Glu
        370                 375                 380
Val Trp Asp Leu Ala Arg Lys Val Thr Ser Ser Gln Ser Glu Phe
385                 390                 395                 400
Asp Gln Asp Gly Asn Cys Leu Ser Ala Gly Arg Val Arg Ile Glu Phe
                405                 410                 415
Asn Asp Gly Ser Ser Ile Thr Glu Ser Val Glu Lys Pro Leu Gly Val
            420                 425                 430
Lys Glu Pro Met Pro Asn Glu Arg Ile Leu His Lys Tyr Arg Thr Leu
        435                 440                 445
Ala Gly Ser Val Thr Asp Glu Ser Arg Val Lys Glu Ile Glu Asp Leu
        450                 455                 460
Val Leu Gly Leu Asp Arg Leu Thr Asp Ile Ser Pro Leu Leu Glu Leu
465                 470                 475                 480
Leu Asn Cys Pro Val Lys Ser Pro Leu Gly Ile
                485                 490

<210> SEQ ID NO 4
<211> LENGTH: 1476
<212> TYPE: DNA
<213> ORGANISM: Aspergillus terreus

<400> SEQUENCE: 4
atgaccaaac aatctgcgga cagcaacgca aagtcaggag ttacgtccga aatatgtcat      60
tgggcatcca acctggccac tgacgacatc ccttcggacg tattagaaag agcaaaatac     120
cttattctcg acggtattgc atgtgcctgg gttggtgcaa gagtgccttg gtcagagaag     180
tatgttcagg caacgatgag ctttgagccg ccgggggcct gcagggtgat ggatatgga      240
cagaaactgg ggcctgttgc agcagccatg accaattccg ctttcataca ggctacggag     300
cttgacgact accacagcga agcccccccta cactctgcaa gcattgtcct tcctgcggtc    360
tttgcagcaa gtgaggtctt agccgagcag ggcaaaacaa tttccggtat agatgttatt     420
ctagccgcca ttgtggggtt tgaatctggc ccacggatcg gcaaagcaat ctacggatcg     480
gacctcttga caacggctg gcattgtgga gctgtgtatg cgctccagc cggtgcgctg      540
gccacaggaa agctcctcgg tctaactcca gactccatgg aagatgctct cggaattgcg     600
tgcacgcaag cctgtggttt aatgtcggcg caatacggag gcatggtaaa gcgtgtgcaa     660
cacggattcg cagcgcgtaa tggtcttctt ggggactgt tggcccatgg tgggtacgag      720
gcaatgaaag gtgtcctgga gagatcttac ggcggtttcc tcaagatgtt caccaagggc     780
```

```
aacggcagag agcctcccta caaagaggag gaagtggtgg ctggtctcgg ttcattctgg    840
cataccttta ctattcgcat caagctctat gcctgctgcg gacttgtcca tggtccagtc    900
gaggctatcg aaaaccttca ggggagatac cccgagctct tgaatagagc caacctcagc    960
aacattcgcc atgttcatgt acagctttca acggcctcga acagtcactg tggatggata   1020
ccagaggaga gacccatcag ttcaatcgca gggcagatga gtgtcgcata cattctcgcc   1080
gtccagctgg tcgaccagca atgtcttttg tcccagtttt ctgagtttga tgacaacctg   1140
gagaggccag aagtttggga tctggccagg aaggttactt catctcaaag cgaagagttt   1200
gatcaagacg gcaactgtct cagtgcgggt cgcgtgagga ttgagttcaa cgatggttct   1260
tctattacgg aaagtgtcga gaagcctctt ggtgtcaaag agcccatgcc aaacgaacgg   1320
attctccaca ataccgaac ccttgctggt agcgtgacga cgaatcccg ggtgaaagag   1380 attgaggatc ttgtcctcgg cctggacagg ctcaccgaca ttagcccatt gctggagctg   1440
ctgaattgcc ccgtgaaatc gccccttggt atataa                              1476
```

<210> SEQ ID NO 5
<211> LENGTH: 492
<212> TYPE: PRT
<213> ORGANISM: Aspergillus terreus

<400> SEQUENCE: 5

```
Met Thr Lys Gln Ser Ala Asp Ser Asn Ala Lys Ser Gly Val Thr Ser
1               5                   10                  15

Glu Ile Cys His Trp Ala Ser Asn Leu Ala Thr Asp Asp Ile Pro Ser
            20                  25                  30

Asp Val Leu Glu Arg Ala Lys Tyr Leu Ile Leu Asp Gly Ile Ala Cys
        35                  40                  45

Ala Trp Val Gly Ala Arg Val Pro Trp Ser Glu Lys Tyr Val Gln Ala
    50                  55                  60

Thr Met Ser Phe Glu Pro Pro Gly Ala Cys Arg Val Ile Gly Tyr Gly
65                  70                  75                  80

Gln Lys Leu Gly Pro Val Ala Ala Ala Met Thr Asn Ser Ala Phe Ile
                85                  90                  95

Gln Ala Thr Glu Leu Asp Asp Tyr His Ser Glu Ala Pro Leu His Ser
            100                 105                 110

Ala Ser Ile Val Leu Pro Ala Val Phe Ala Ala Ser Glu Val Leu Ala
        115                 120                 125

Glu Gln Gly Lys Thr Ile Ser Gly Ile Asp Val Ile Leu Ala Ala Ile
    130                 135                 140

Val Gly Phe Glu Ser Gly Pro Arg Ile Gly Lys Ala Ile Tyr Gly Ser
145                 150                 155                 160

Asp Leu Leu Asn Asn Gly Trp His Cys Gly Ala Val Tyr Gly Ala Pro
                165                 170                 175

Ala Gly Ala Leu Ala Thr Gly Lys Leu Leu Gly Leu Thr Pro Asp Ser
            180                 185                 190

Met Glu Asp Ala Leu Gly Ile Ala Cys Thr Gln Ala Cys Gly Leu Met
        195                 200                 205

Ser Ala Gln Tyr Gly Gly Met Val Lys Arg Val Gln His Gly Phe Ala
    210                 215                 220

Ala Arg Asn Gly Leu Leu Gly Leu Leu Ala His Gly Gly Tyr Glu
225                 230                 235                 240

Ala Met Lys Gly Val Leu Glu Arg Ser Tyr Gly Gly Phe Leu Lys Met
                245                 250                 255
```

```
Phe Thr Lys Gly Asn Gly Arg Glu Pro Pro Tyr Lys Glu Glu Val
            260                 265                 270
Val Ala Gly Leu Gly Ser Phe Trp His Thr Phe Thr Ile Arg Ile Lys
    275                 280                 285
Leu Tyr Ala Cys Cys Gly Leu Val His Gly Pro Val Glu Ala Ile Glu
        290                 295                 300
Asn Leu Gln Gly Arg Tyr Pro Glu Leu Leu Asn Arg Ala Asn Leu Ser
305                 310                 315                 320
Asn Ile Arg His Val His Val Gln Leu Ser Thr Ala Ser Asn Ser His
                325                 330                 335
Cys Gly Trp Ile Pro Glu Glu Arg Pro Ile Ser Ile Ala Gly Gln
            340                 345                 350
Met Ser Val Ala Tyr Ile Leu Ala Val Gln Leu Val Asp Gln Cys
        355                 360                 365
Leu Leu Ser Gln Phe Ser Glu Phe Asp Asp Asn Leu Glu Arg Pro Glu
    370                 375                 380
Val Trp Asp Leu Ala Arg Lys Val Thr Ser Gln Ser Glu Glu Phe
385                 390                 395                 400
Asp Gln Asp Gly Asn Cys Leu Ser Ala Gly Arg Val Arg Ile Glu Phe
                405                 410                 415
Asn Asp Gly Ser Ser Ile Thr Glu Ser Val Glu Lys Pro Leu Gly Val
            420                 425                 430
Lys Glu Pro Met Pro Asn Glu Arg Ile Leu His Lys Tyr Arg Thr Leu
        435                 440                 445
Ala Gly Ser Val Thr Asp Glu Ser Arg Val Lys Glu Ile Glu Asp Leu
    450                 455                 460
Val Leu Gly Leu Asp Arg Leu Thr Asp Ile Ser Pro Leu Leu Glu Leu
465                 470                 475                 480
Leu Asn Cys Pro Val Lys Ser Pro Leu Gly Ile Lys
                485                 490

<210> SEQ ID NO 6
<211> LENGTH: 1479
<212> TYPE: DNA
<213> ORGANISM: Aspergillus terreus

<400> SEQUENCE: 6
atgaccaaac aatctgcgga cagcaacgca aagtcaggag ttacgtccga aatatgtcat      60
tgggcatcca acctggccac tgacgacatc ccttcggacg tattagaaag agcaaaatac    120
cttattctcg acggtattgc atgtgcctgg gttggtgcaa gagtgccttg gtcagagaag    180
tatgttcagg caacgatgag ctttgagccg ccgggggcct gcagggtgat ggatatgga    240 cagaaactgg ggcctgttgc agcagccatg accaattccg ctttcataca ggctacggag    300
cttgacgact accacagcga agccccccta cactctgcaa gcattgtcct tcctgcggtc    360
tttgcagcaa gtgaggtctt agccgagcag ggcaaaacaa tttccggtat agatgttatt    420
ctagccgcca ttgtgggggtt tgaatctggc ccacggatcg gcaaagcaat ctacggatcg    480
gacctcttga caacggctg cattgtggga ctgtgtatg cgctccagc cggtgcgctg    540 gccacaggaa agctcctcgg tctaactcca gactccatgg aagatgctct cggaattgcg    600
tgcacgcaag cctgtggttt aatgtcggcg caatacggag gcatggtaaa gcgtgtgcaa    660
cacggattcg cagcgcgtaa tggtcttctt gggggactgt tggcccatgg tgggtacgag    720
gcaatgaaag gtgtcctgga gagatcttac ggcggtttcc tcaagatgtt caccaagggc    780
```

```
aacggcagag agcctcccta caaagaggag gaagtggtgg ctggtctcgg ttcattctgg    840
cataccttta ctattcgcat caagctctat gcctgctgcg gacttgtcca tggtccagtc    900
gaggctatcg aaaaccttca ggggagatac cccgagctct tgaatagagc caacctcagc    960
aacattcgcc atgttcatgt acagctttca acggcctcga acagtcactg tggatggata   1020
ccagaggaga gacccatcag ttcaatcgca gggcagatga gtgtcgcata cattctcgcc   1080
gtccagctgg tcgaccagca atgtcttttg tcccagtttt ctgagtttga tgacaacctg   1140
gagaggccag aagtttggga tctggccagg aaggttactt catctcaaag cgaagagttt   1200
gatcaagacg gcaactgtct cagtgcgggt cgcgtgagga ttgagttcaa cgatggttct   1260
tctattacgg aaagtgtcga gaagcctctt ggtgtcaaag agcccatgcc aaacgaacgg   1320
attctccaca ataccgaacc cttgctggt agcgtgacgg acgaatcccg ggtgaaagag   1380
attgaggatc ttgtcctcgg cctggacagg ctcaccgaca ttagcccatt gctggagctg   1440
ctgaattgcc ccgtgaaatc gcccctgggt ataaaataa                         1479
```

```
<210> SEQ ID NO 7
<211> LENGTH: 491
<212> TYPE: PRT
<213> ORGANISM: Aspergillus terreus

<400> SEQUENCE: 7

Met Thr Lys Gln Ser Ala Asp Ser Asn Ala Lys Ser Gly Val Thr Ser
1               5                   10                  15

Glu Ile Cys His Trp Ala Ser Asn Leu Ala Thr Asp Asp Ile Pro Ser
            20                  25                  30

Asp Val Leu Glu Arg Ala Lys Tyr Leu Ile Leu Asp Gly Ile Ala Cys
        35                  40                  45

Ala Trp Val Gly Ala Arg Val Pro Trp Ser Glu Lys Tyr Val Gln Ala
    50                  55                  60

Thr Met Ser Phe Glu Pro Pro Gly Ala Cys Arg Val Ile Gly Tyr Gly
65                  70                  75                  80

Gln Lys Leu Gly Pro Val Ala Ala Ala Met Thr Asn Ser Ala Phe Ile
                85                  90                  95

Gln Ala Thr Glu Leu Asp Asp Tyr His Ser Glu Ala Pro Leu His Ser
            100                 105                 110

Ala Ser Ile Val Leu Pro Ala Val Phe Ala Ala Ser Glu Val Leu Ala
        115                 120                 125

Glu Gln Gly Lys Thr Ile Ser Gly Ile Asp Val Ile Leu Ala Ala Ile
    130                 135                 140

Val Gly Phe Glu Ser Gly Pro Arg Ile Gly Lys Ala Ile Tyr Gly Ser
145                 150                 155                 160

Asp Leu Leu Asn Asn Gly Trp His Cys Gly Ala Val Tyr Gly Ala Pro
                165                 170                 175

Ala Gly Ala Leu Ala Thr Gly Lys Leu Leu Gly Leu Thr Pro Asp Ser
            180                 185                 190

Met Glu Asp Ala Leu Gly Ile Ala Cys Thr Gln Ala Cys Gly Leu Met
        195                 200                 205

Ser Ala Gln Tyr Gly Gly Met Val Lys Arg Val Gln His Gly Phe Ala
    210                 215                 220

Ala Arg Asn Gly Leu Leu Gly Leu Leu Ala His Gly Gly Tyr Glu
225                 230                 235                 240

Ala Met Lys Gly Val Leu Glu Arg Ser Tyr Gly Gly Phe Leu Lys Met
                245                 250                 255
```

```
Phe Thr Lys Gly Asn Gly Arg Glu Pro Pro Tyr Lys Glu Glu Val
            260                 265                 270
Val Ala Gly Leu Gly Ser Phe Trp His Thr Phe Thr Ile Arg Ile Lys
        275                 280                 285
Leu Tyr Ala Cys Cys Gly Leu Val His Gly Pro Val Glu Ala Ile Glu
        290                 295                 300
Asn Leu Gln Gly Arg Tyr Pro Glu Leu Leu Asn Arg Ala Asn Leu Ser
305                 310                 315                 320
Asn Ile Arg His Val His Val Gln Leu Ser Thr Ala Ser Asn Ser His
            325                 330                 335
Cys Gly Trp Ile Pro Glu Glu Arg Pro Ile Ser Ile Ala Gly Gln
            340                 345                 350
Met Ser Val Ala Tyr Ile Leu Ala Val Gln Leu Val Asp Gln Gln Cys
        355                 360                 365
Leu Leu Ser Gln Phe Ser Glu Phe Asp Asp Asn Leu Glu Arg Pro Glu
        370                 375                 380
Val Trp Asp Leu Ala Arg Lys Val Thr Ser Ser Gln Ser Glu Glu Phe
385                 390                 395                 400
Asp Gln Asp Gly Asn Cys Leu Ser Ala Gly Arg Val Arg Ile Glu Phe
                405                 410                 415
Asn Asp Gly Ser Ser Ile Thr Glu Ser Val Glu Lys Pro Leu Gly Val
            420                 425                 430
Lys Glu Pro Met Pro Asn Glu Arg Ile Leu His Lys Tyr Arg Thr Leu
        435                 440                 445
Ala Gly Ser Val Thr Asp Glu Ser Arg Val Lys Glu Ile Glu Asp Leu
        450                 455                 460
Val Leu Gly Leu Asp Arg Leu Thr Asp Ile Ser Pro Leu Leu Glu Leu
465                 470                 475                 480
Leu Asn Cys Pro Val Lys Ser Pro Phe Gly Ile
                485                 490

<210> SEQ ID NO 8
<211> LENGTH: 1476
<212> TYPE: DNA
<213> ORGANISM: Aspergillus terreus

<400> SEQUENCE: 8
atgaccaaac aatctgcgga cagcaacgca aagtcaggag ttacgtccga aatatgtcat    60
tgggcatcca acctggccac tgacgacatc ccttcggacg tattagaaag agcaaaatac   120
cttattctcg acggtattgc atgtgcctgg gttggtgcaa gagtgccttg gtcagagaag   180
tatgttcagg caacgatgag ctttgagccg ccgggggcct gcagggtgat tggatatgga   240
cagaaactgg ggcctgttgc agcagccatg accaattccg ctttcataca ggctacggag   300
cttgacgact accacagcga agccccccta cactctgcaa gcattgtcct tcctgcggtc   360
tttgcagcaa gtgaggtctt agccgagcag ggcaaaacaa tttccggtat agatgttatt   420
ctagccgcca ttgtgggggtt tgaatctggc ccacggatcg gcaaagcaat ctacggatcg   480
gacctcttga caacggctg gcattgtgga gctgtgtatg gcgctccagc cggtgcgctg   540
gccacaggaa agctcctcgg tctaactcca gactccatgg aagatgctct cggaattgcg   600
tgcacgcaag cctgtggttt aatgtcggcg caatacggag gcatggtaaa gcgtgtgcaa   660
cacggattcg cagcgcgtaa tggtcttctt gggggactgt tggcccatgg tgggtacgag   720
gcaatgaaag gtgtcctgga gagatcttac ggcggtttcc tcaagatgtt caccaagggc   780
aacggcagag agcctcccta caagaggag gaagtggtgg ctggtctcgg ttcattctgg   840
```

-continued

```
cataccttta ctattcgcat caagctctat gcctgctgcg gacttgtcca tggtccagtc    900
gaggctatcg aaaaccttca ggggagatac cccgagctct tgaatagagc caacctcagc    960
aacattcgcc atgttcatgt acagctttca acggcctcga acagtcactg tggatggata   1020
ccagaggaga gacccatcag ttcaatcgca gggcagatga gtgtcgcata cattctcgcc   1080
gtccagctgg tcgaccagca atgtcttttg tcccagtttt ctgagtttga tgacaacctg   1140
gagaggccag aagtttggga tctggccagg aaggttactt catctcaaag cgaagagttt   1200
gatcaagacg gcaactgtct cagtgcgggt cgcgtgagga ttgagttcaa cgatggttct   1260
tctattacgg aaagtgtcga gaagcctctt ggtgtcaaag agcccatgcc aaacgaacgg   1320
attctccaca ataccgaacc ccttgctggt agcgtgacgg acgaatcccg ggtgaaagag   1380
attgaggatc ttgtcctcgg cctggacagg ctcaccgaca ttagcccatt gctggagctg   1440
ctgaattgcc ccgtgaaatc gcccttggt atataa                              1476
```

<210> SEQ ID NO 9
<211> LENGTH: 492
<212> TYPE: PRT
<213> ORGANISM: Artificial
<220> FEATURE:
<223> OTHER INFORMATION: Laboratory generated variant based upon the cis-aconitate decarboxylase of Aspergillus terreus
<220> FEATURE:
<221> NAME/KEY: Mutation
<222> LOCATION: (441)..(492)

<400> SEQUENCE: 9

Met Thr Lys Gln Ser Ala Asp Ser Asn Ala Lys Ser Gly Val Thr Ser
1               5                   10                  15

Glu Ile Cys His Trp Ala Ser Asn Leu Ala Thr Asp Asp Ile Pro Ser
            20                  25                  30

Asp Val Leu Glu Arg Ala Lys Tyr Leu Ile Leu Asp Gly Ile Ala Cys
        35                  40                  45

Ala Trp Val Gly Ala Arg Val Pro Trp Ser Glu Lys Tyr Val Gln Ala
    50                  55                  60

Thr Met Ser Phe Glu Pro Pro Gly Ala Cys Arg Val Ile Gly Tyr Gly
65                  70                  75                  80

Gln Lys Leu Gly Pro Val Ala Ala Ala Met Thr Asn Ser Ala Phe Ile
                85                  90                  95

Gln Ala Thr Glu Leu Asp Asp Tyr His Ser Glu Ala Pro Leu His Ser
            100                 105                 110

Ala Ser Ile Val Leu Pro Ala Val Phe Ala Ala Ser Glu Val Leu Ala
        115                 120                 125

Glu Gln Gly Lys Thr Ile Ser Gly Ile Asp Val Ile Leu Ala Ala Ile
    130                 135                 140

Val Gly Phe Glu Ser Gly Pro Arg Ile Gly Lys Ala Ile Tyr Gly Ser
145                 150                 155                 160

Asp Leu Leu Asn Asn Gly Trp His Cys Gly Ala Val Tyr Gly Ala Pro
                165                 170                 175

Ala Gly Ala Leu Ala Thr Gly Lys Leu Leu Gly Leu Thr Pro Asp Ser
            180                 185                 190

Met Glu Asp Ala Leu Gly Ile Ala Cys Thr Gln Ala Cys Gly Leu Met
        195                 200                 205

Ser Ala Gln Tyr Gly Gly Met Val Lys Arg Val Gln His Gly Phe Ala
    210                 215                 220

Ala Arg Asn Gly Leu Leu Gly Gly Leu Leu Ala His Gly Gly Tyr Glu

```
                 225                 230                 235                 240
        Ala Met Lys Gly Val Leu Glu Arg Ser Tyr Gly Gly Phe Leu Lys Met
                        245                 250                 255

Phe Thr Lys Gly Asn Gly Arg Glu Pro Pro Tyr Lys Glu Glu Val
                        260                 265                 270

Val Ala Gly Leu Gly Ser Phe Trp His Thr Phe Thr Ile Arg Ile Lys
                    275                 280                 285

Leu Tyr Ala Cys Cys Gly Leu Val His Gly Pro Val Glu Ala Ile Glu
                    290                 295                 300

Asn Leu Gln Gly Arg Tyr Pro Glu Leu Leu Asn Arg Ala Asn Leu Ser
        305                 310                 315                 320

Asn Ile Arg His Val His Val Gln Leu Ser Thr Ala Ser Asn Ser His
                        325                 330                 335

Cys Gly Trp Ile Pro Glu Glu Arg Pro Ile Ser Ser Ile Ala Gly Gln
                        340                 345                 350

Met Ser Val Ala Tyr Ile Leu Ala Val Gln Leu Val Asp Gln Gln Cys
                        355                 360                 365

Leu Leu Ser Gln Phe Ser Glu Phe Asp Asp Asn Leu Glu Arg Pro Glu
                    370                 375                 380

Val Trp Asp Leu Ala Arg Lys Val Thr Ser Ser Gln Ser Glu Glu Phe
        385                 390                 395                 400

Asp Gln Asp Gly Asn Cys Leu Ser Ala Gly Arg Val Arg Ile Glu Phe
                        405                 410                 415

Asn Asp Gly Ser Ser Ile Thr Glu Ser Val Glu Lys Pro Leu Gly Val
                        420                 425                 430

Lys Glu Pro Met Pro Asn Glu Arg Phe Pro Arg Gly Glu Pro Gly Gln
                        435                 440                 445

Pro Arg Phe Cys Glu Asn Ala Gly Lys Ser Gly Ser Gly Asp Gly Gly
                    450                 455                 460

Ala Glu Leu His Ser Gln Pro Arg Gly Thr Thr Thr Gly Gly Gln Thr
        465                 470                 475                 480

Val Val Ala Asp Trp Arg Cys His Leu Gln Ser Gly
                    485                 490

<210> SEQ ID NO 10
<211> LENGTH: 1479
<212> TYPE: DNA
<213> ORGANISM: Artificial
<220> FEATURE:
<223> OTHER INFORMATION: Laboratory generated variant encoding mutant
      cis-aconitate decarboxylase of Aspergillus terreus

<400> SEQUENCE: 10
atgaccaagc agtctgctga ttccaacgcg aagtctggtg tgacctctga gatctgtcac      60
tgggcgtcta atctcgccac tgatgatatc ccgagcgacg ttctggagcg tgcaaaatac     120
ctgatcctgg atggtatcgc gtgcgcgtgg gtaggtgctc tgtcccatg gtctgaaaaa      180 tacgttcaag cgaccatgtc tttcgaacct ccgggtgcgt gtcgtgtcat cggttacggc     240
cagaaactgg gtccggtagc ggctgccatg acgaactctg catttattca ggcgaccgaa     300
ctcgatgact atcactctga agcgccgctg cattccgcgt ctatcgttct cccggcagtt     360
ttcgcggcga gcgaagtact ggccgaacag ggtaaaacca tctctggtat tgacgtgatt     420
ctggctgcga tcgttggttt cgagagcggt cctcgcatcg caaagcgat ctacggttct      480 gacctcctga caacggctg gcactgcggt gcggtatatg cgcaccggc tggtgcgctc      540 gcaactggta agctcctggg cctcacgccg acagcatgg aagatgcact gggtattgcc     600
```

```
tgcacgcaag catgcggcct catgtccgcg cagtatggtg gcatggttaa acgtgttcag    660
cacggtttcg cagcgcgtaa tggtctcctc ggtggcctcc tggctcacgg cggctacgag    720
gcgatgaaag gtgttctcga gcgttcttac ggtggcttcc tgaagatgtt caccaagggc    780
aacggtcgtg aaccgccgta caagaagaa gaggttgtgg ctggtctggg tagcttctgg     840
cacaccttca ccattcgtat caaactgtac gcgtgctgcg gtctcgtaca cggtcctgtt    900
gaagccattg aaaacctcca gggtcgttac ccggaactgc tcaatcgtgc taacctgtct    960
aacatccgcc acgttcacgt acaactctct accgcgagca actcccactg tggttggatc   1020
ccagaagagc gcccaatctc ttctatcgcg ggtcaaatgt ctgtcgcata tcctcgcc     1080 gttcagctcg ttgaccaaca gtgtctgctc agccagttct ccgagtttga cgataatctg   1140
gaacgcccgg aagtgtggga cctggcacgt aaggttacca gctctcaatc tgaggagttc   1200
gaccaggacg gtaactgtct ctctgccggt cgcgtccgta ttgagttcaa cgacggctcc   1260
tccatcaccg aatccgttga gaagccgctc ggtgtaaagg aaccaatgcc aaatgaacgc   1320
ttcccgcgtg gtgaaccagg ccagccacgt ttctgcgaaa acgcgggaaa agtggaagc   1380 ggcgatggcg gagctgaatt acattcccaa ccgcgtggca caacaactgg cgggcaaaca   1440
gtcgttgctg attggcgttg ccacctccag tctggctaa                          1479
```

<210> SEQ ID NO 11
<211> LENGTH: 1473
<212> TYPE: DNA
<213> ORGANISM: Artificial
<220> FEATURE:
<223> OTHER INFORMATION: Laboratory generated variant encoding wild type
      cis-aconitate decarboxylase of Aspergillus terreus

<400> SEQUENCE: 11

```
atgaccaagc agtctgctga ttccaacgcg aagtctggtg tgacctctga gatctgtcac     60
tgggcgtcta atctcgccac tgatgatatc ccgagcgacg ttctggagcg tgcaaaatac    120
ctgatcctgg atggtatcgc gtgcgcgtgg gtaggtgctc gtgtcccatg gtctgaaaaa    180
tacgttcaag cgaccatgtc tttcgaacct ccgggtgcgt gtcgtgtcat cggttacggc    240
cagaaactgg gtccggtagc ggctgccatg acgaactctg catttattca ggcgaccgaa    300
ctcgatgact atcactctga gcgccgctg cattccgcgt ctatcgttct cccggcagtt     360
ttcgcggcga gcgaagtact ggccgaacag ggtaaaacca tctctggtat tgacgtgatt    420
ctggctgcga tcgttggttt cgagagcggt cctcgcatcg gcaaagcgat ctacggttct    480
gacctcctga caacggctg gcactgcggt gcggtatatg gcgcaccggc tggtgcgctc    540
gcaactggta gctcctggg cctcacgccg gacagcatgg aagatgcact gggtattgcc     600
tgcacgcaag catgcggcct catgtccgcg cagtatggtg gcatggttaa acgtgttcag    660
cacggtttcg cagcgcgtaa tggtctcctc ggtggcctcc tggctcacgg cggctacgag    720
gcgatgaaag gtgttctcga gcgttcttac ggtggcttcc tgaagatgtt caccaagggc    780
aacggtcgtg aaccgccgta caagaagaa gaggttgtgg ctggtctggg tagcttctgg     840
cacaccttca ccattcgtat caaactgtac gcgtgctgcg gtctcgtaca cggtcctgtt    900
gaagccattg aaaacctcca gggtcgttac ccggaactgc tcaatcgtgc taacctgtct    960
aacatccgcc acgttcacgt acaactctct accgcgagca actcccactg tggttggatc   1020
ccagaagagc gcccaatctc ttctatcgcg ggtcaaatgt ctgtcgcata tcctcgcc     1080 gttcagctcg ttgaccaaca gtgtctgctc agccagttct ccgagtttga cgataatctg   1140
```

```
gaacgcccgg aagtgtggga cctggcacgt aaggttacca gctctcaatc tgaggagttc    1200
gaccaggacg gtaactgtct ctctgccggt cgcgtccgta ttgagttcaa cgacggctcc    1260
tccatcaccg aatccgttga gaagccgctc ggtgtaaagg aaccaatgcc aaatgaacgc    1320
atcctgcaca ataccgtac cctggcgggt tctgtaacgg acgaaagccg tgttaaggag    1380
atcgaggatc tcgtgctcgg cctggaccgt ctgaccgata ttagcccgct cctcgagctg    1440
ctgaattgtc cggttaaatc cccactggtt taa                                 1473
```

```
<210> SEQ ID NO 12
<211> LENGTH: 24
<212> TYPE: DNA
<213> ORGANISM: Artificial
<220> FEATURE:
<223> OTHER INFORMATION: Synthetic primer

<400> SEQUENCE: 12
cagccatgac caattccgct ttca                                            24

<210> SEQ ID NO 13
<211> LENGTH: 24
<212> TYPE: DNA
<213> ORGANISM: Artificial
<220> FEATURE:
<223> OTHER INFORMATION: Synthetic primer

<400> SEQUENCE: 13
aagacctcac ttgctgcaaa gacc                                            24

<210> SEQ ID NO 14
<211> LENGTH: 20
<212> TYPE: DNA
<213> ORGANISM: Artificial
<220> FEATURE:
<223> OTHER INFORMATION: Synthetic primer

<400> SEQUENCE: 14
ttgtggagct gtgtatggcg                                                 20

<210> SEQ ID NO 15
<211> LENGTH: 16
<212> TYPE: DNA
<213> ORGANISM: Artificial
<220> FEATURE:
<223> OTHER INFORMATION: Synthetic primer

<400> SEQUENCE: 15
gttggcccat ggtggg                                                     16

<210> SEQ ID NO 16
<211> LENGTH: 20
<212> TYPE: DNA
<213> ORGANISM: Artificial
<220> FEATURE:
<223> OTHER INFORMATION: Synthetic primer

<400> SEQUENCE: 16
catggctgct gcaacaggcc                                                 20

<210> SEQ ID NO 17
<211> LENGTH: 29
<212> TYPE: DNA
<213> ORGANISM: Artificial
<220> FEATURE:
<223> OTHER INFORMATION: Synthetic primer
```

```
<400> SEQUENCE: 17
actcatatga tgaccaaaca atctgcgga                                              29

<210> SEQ ID NO 18
<211> LENGTH: 30
<212> TYPE: DNA
<213> ORGANISM: Artificial
<220> FEATURE:
<223> OTHER INFORMATION: Synthetic primer

<400> SEQUENCE: 18
tacggatcct ataccaaggg gcgatttcac                                             30

<210> SEQ ID NO 19
<211> LENGTH: 31
<212> TYPE: DNA
<213> ORGANISM: Artificial
<220> FEATURE:
<223> OTHER INFORMATION: Synthetic primer

<400> SEQUENCE: 19
tacggatcct tttataccca ggggcgattt c                                           31

<210> SEQ ID NO 20
<211> LENGTH: 31
<212> TYPE: DNA
<213> ORGANISM: Artificial
<220> FEATURE:
<223> OTHER INFORMATION: Synthetic primer

<400> SEQUENCE: 20
tacggatcct ataccaaagg gcgatttcac g                                           31

<210> SEQ ID NO 21
<211> LENGTH: 20
<212> TYPE: DNA
<213> ORGANISM: Artificial
<220> FEATURE:
<223> OTHER INFORMATION: Synthetic primer

<400> SEQUENCE: 21
ctcagcttcc tttcgggctt                                                        20

<210> SEQ ID NO 22
<211> LENGTH: 15
<212> TYPE: DNA
<213> ORGANISM: Artificial
<220> FEATURE:
<223> OTHER INFORMATION: Synthetic primer

<400> SEQUENCE: 22
cgcacctgtg gcgcc                                                             15
```